United States Patent [19]

Connor et al.

[11] 4,123,536
[45] Oct. 31, 1978

[54] DIALKYL ({[3-(ALKOXYCARBONYL)-1,4-DIHYDRO-4-OXO-8-QUINOLINYL]AMINO}METHYLENE)PROPANEDIOATES

[75] Inventors: David T. Connor, Ann Arbor, Mich.; Patricia A. Young, Madison, N.J.; Maximilian Von Strandtmann, New Castle, Del.

[73] Assignee: Warner-Lambert Company, Morris Plains, N.J.

[21] Appl. No.: 860,526

[22] Filed: Dec. 14, 1977

[51] Int. Cl.² .................. A61K 31/47; C07D 215/56
[52] U.S. Cl. ..................... 424/258; 260/287 AN; 260/287 CF; 560/22; 560/44
[58] Field of Search ............ 260/287 AN; 424/258

[56] References Cited

U.S. PATENT DOCUMENTS 3,790,577  2/1974  Waring ................................ 424/258

OTHER PUBLICATIONS

Snyder et al., "J. Am. Chem. Soc." 68:1320-1322, (1946).

*Primary Examiner*—Donald G. Daus
*Assistant Examiner*—David E. Wheeler
*Attorney, Agent, or Firm*—Albert H. Graddis; Frank S. Chow; Anne M. Kelly

[57] ABSTRACT

The present invention relates to dialkyl ({[3-(alkoxycarbonyl)-1,4-dihydro-4-oxo-8-quinolinyl]amino}methylene)-propanedioates having the following structural formula:

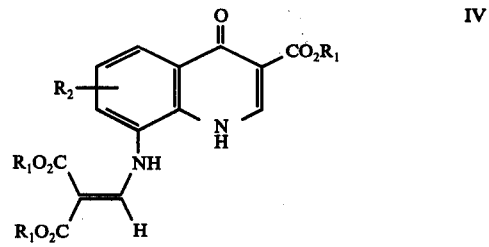

wherein $R_1$ is lower alkyl; and $R_2$ is hydrogen, halogen, lower alkyl or nitro.

These compounds exhibit antibacterial activity against gram positive and gram negative bacteria and are therefore useful in the treatment of bacterial infections caused by these organisms.

7 Claims, No Drawings

DIALKYL ({[3-(ALKOXYCARBONYL)-1,4-DIHYDRO-4-OXO-8-QUINOLINYL]AMINO}METHYLENE)PROPANEDIOATES

The present invention relates to dialkyl ({[3-(alkoxycarbonyl)-1,4-dihydro-4-oxo-8-quinolinyl]amino}-methylene)propanedioates which have the following structural formula:

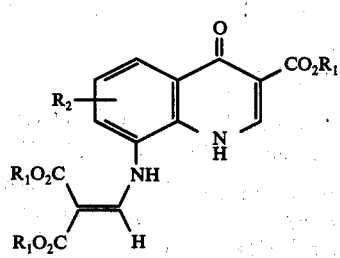

wherein $R_1$ is lower alkyl; and $R_2$ is hydrogen, halogen, lower alkyl or nitro.

Also included within the scope of this invention is a novel process for preparing compounds having the formula IV.

The compounds of the present invention having the formula IV exhibit antibacterial activity against gram positive and gram negative bacteria. For example, diethyl ({[3-ethoxycarbonyl)-1,4-dihydro-4-oxo-8-quinolinyl]amino}methylene)propanedioate, which is the compound of Example 3, exhibits a minimal inhibitory concentration of 15.6 micrograms per milliliter against S. aureus; and a minimal inhibitory concentration of 125 micograms per milliliter against E. coli. The compounds of the invention having the formula IV are, therefore, useful in the treatment of systemic or topical infections caused by gram positive or gram negative bacteria. The compounds of the invention having the formula IV can be administered orally, parenterally or topically to various mammals such as dogs, cats and guinea pigs afflicted with bacterial diseases.

In order to use the compounds of the invention having the formula IV, they may be formulated with inert excipients into various dosage forms for oral, parenteral and topical administration by methods well known to those skilled in the pharmacists's art. Tablets, capsules, powders, solutions, suspensions, ointments, gels and creams are included among these dosage forms. When formulated with a topically acceptable vehicle such as talc or petrolatum, the active ingredient may be present in an amount of from about 0.1% to about 5%.

To treat systemic infections caused by susceptible organisms, the compounds of the invention are formulated into dosage forms with inert diluents such as lactose. The active ingredient in the tablet may vary from 25–250 milligrams per tablet.

The compounds of the invention having IV are prepared according to the following reaction scheme.

SCHEME 1

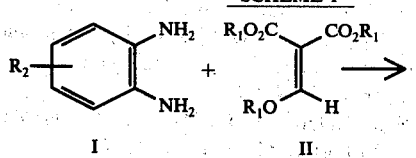

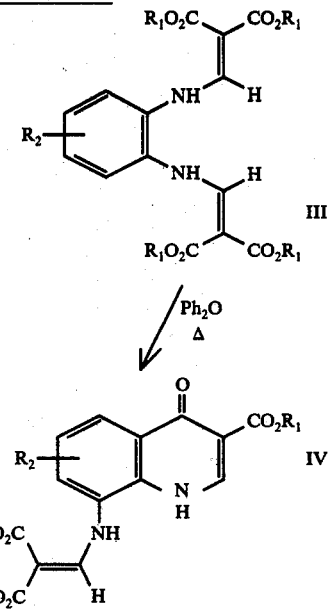

Referring to the reaction scheme above, an appropriately substituted ortho-phenylenediamine (I) is reacted with a dialkyl alkoxymethylenemalonate (II) to form the intermediate tetralkyl [substituted-1,2-phenylenebis-(aminomethylene)]-dimalonate (III) which is then refluxed in diphenyl ether under nitrogen for from 15 to 30 minutes to obtain the final compounds of the invention having the formula IV.

The starting ortho-phenylenediamines having the formula I are available from Aldrich Chemical Company. The intermediate compounds III wherein $R_2$ is hydrogen, are prepared by the method of H. R. Snyder and H. E. Freier described in J. Am. Chem. Soc. 68: 1320-2 (1946), by heating ortho-phenylenediamine and ethoxymethylenemalonic ester on a steam bath for four hours. Similarly, intermediate compound II wherein $R_2$ is lower alkyl may be prepared by the method of W. S. Waring described in British Pat. No. 1,335,623, by heating 3,4-diamino-1-n-butyl benzene with the dimethyl ester of methoxymethylenemalonic acid for three hours on a steam bath.

According to the prior art, i.e., aformentioned Synder, et al. and British Pat. No. 1,336,623, the intermediate III, upon refluxing, ring closes to form the tricyclic phenanthroline. No intermediate bicyclic quinolines are identified or isolated in the prior art. According to this invention, it has been found, quite surprisingly that the bicyclic quinoline, (i.e., the compound having the formula IV is formed when compound III is refluxed under nitrogen and this bicyclic quinoline compound can be isolated.

In the above formulas I through IV, the term lower alkyl is meant to include lower alkyl radicals having from one to seven carbon atoms, preferably one to four carbon atoms, for example, methyl, ethyl, propyl, isopropyl, butyl, isobutyl and the like. Halogen is meant to include all four members, i.e., bromine, iodine, fluorine and chlorine.

In order to further illustrate the invention, the following examples are provided:

EXAMPLE 1

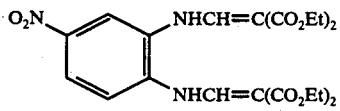

Tetraethyl [4-nitro-1,2-phenylenebis(aminomethylene)]dimalonate.

A solution of 4-nitro-o-phenylenediamine (20g, 0.131 mole) in diethyl ethoxymethylenemalonate (110 ml) is heated at 140° C under nitrogen for 3.5 hours, cooled, and diluted with petroleum ether. The product cyrstallizes out and is filtered off. Recrystallization from ethyl acetate gives yellow crystals (57.5g.90%), mp. 148°–151° C.

ANALYSIS: Calcd. for $C_{22}H_{27}N_3O_{10}$: C, 53.54; H, 5.52; N, 8.52. Found: C, 53.51; H, 5.65; N, 8.48.

EXAMPLE 2

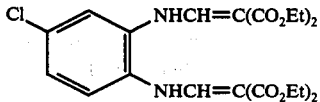

Tetraethyl [4-chloro-1,2-phenylenebis(aminomethylene)]dimalonate.

Prepared by the method described in Example 1 from 4-chloro-o-phenylenediamine (20g, 0.14 mole). Recrystallization from hexane gives off-white cyrstals (42.3g,63%), mp 90°–92° C.

ANALYSIS: Calcd. for $C_{22}H_{27}ClN_2O_8$: C, 54.72; H, 5.64; N, 5.80; Cl, 7.34. Found: C, 54.78; H, 5.65; N, 5.72; Cl, 7.42.

EXAMPLE 3

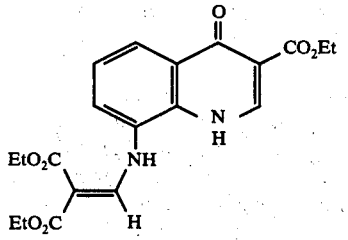

Diethyl ({[3-(ethoxycarbonyl)-1,4-dihydrio-4-oxo-8-quinolinyl]amino}methylene)propanedioate.

A solution of tetraethyl [1,2-phenylenebis(aminomethylene)]dimalonate (15 g, 0.033 mole) in diphenyl ether (250 ml) is refluxed under nitrogen for 30 minutes, cooled and poured into petrolium ether (500 ml.). A crystalline product precipitates out. Weight of product 10.1g (75%) mp 148°–150° C.

ANALYSIS: Calcd. for $C_{20}H_{22}N_2O_7$: C, 59.69; H, 5.51; N, 6.96. Found: C, 59.68; H, 5.46; N, 6.95.

EXAMPLE 4

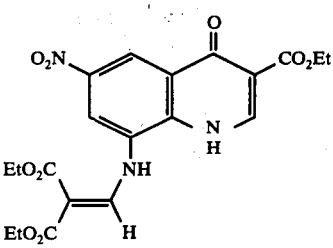

Diethyl ({[3-(ethoxycarbonyl)-1,4-dihydro-6-nitro-4-oxo-8-quinolinyl]amino}methylene)propanedioate.

Prepared from tetraethyl [4-nitro-1,2-phenylenebis(aminomethylene)]dimalonate (20g, 0.04 mole) by the general method described in Example 3. Recrystallization from methanolchloroform gives brown crystals (6.5g, 36%) mp 150°–160° C. (dec.).

ANALYSIS: Calcd. for $C_{20}H_{21}N_3O_9$: C, 53.69; H, 4.73; N, 9.39. Found: C, 54.00; H, 4.45; N, 9.82.

EXAMPLE 5

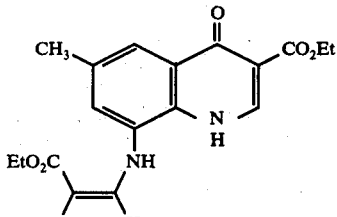

A

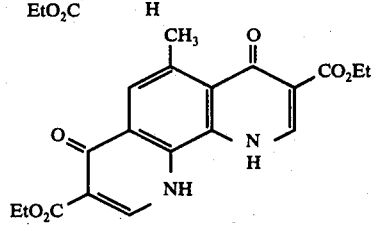

B (A)— Diethyl ({[3-ethoxycarbonyl)-1,4-dihydro-6-methyl-4-oxo-8-quinolinyl]amino}methylene)propanedioate; and (B)— Diethyl 1,4,7,10-tetrahydro-5-methyl-4,7-dioxo-1,10-phenanthroline-3,8-dicarboxylate.

A solution of tetraethyl [4-methyl-1,2-phenylenebis(aminomethylene)]dimalonate (9.2g, 0.02 mole) in diphenyl ether (100 ml) is refluxed under nitrogen for 15 minutes, cooled, and diluted with petroleum ether. Diester (B) crystallizes out and is recrystallized from ethanol-chloroform to give off-white crystals (3.9g, 47%) mp 295°–300° C. (dec).

ANALYSIS: Calcd. for $C_{19}H_{18}N_2O_6$: C, 61.62; H, 4.90; N, 7.56. Found: C, 61.64; H, 4.92; N, 7.63.

A second crop triester (A) crystallizes out and is recrystallized from ethanol to give pale yellow crystals (0.2g, 2.5%) mp 137°–141° C.

ANALYSIS: Calcd. for $C_{21}H_{24}N_2O_7$: C, 60.56; H, 5.81; N, 6.73. Found C, 60.68; H, 5.71; N, 6.87.

EXAMPLE 6

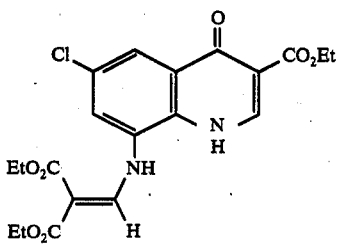

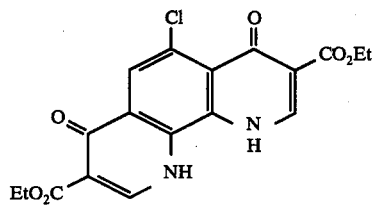

(A)— Diethyl ({[3-(ethoxycarbonyl)-1,4-dihydro-6-chloro-4-oxo-8-quinolinyl]amino}methylene)propanedioate; and (B)— Diethyl 1,4,7,10-tetrahydro-5-chloro-4,7-dioxo-1,10-phenanthroline-3,8-dicarboxylate.

A solution of tetraethyl [4-chloro-1,2-phenylenebis(aminomethylene)]dimalonate (25g, 0.052 mole) in diphenyl ether (100 ml) is refluxed under nitrogen for 30 minutes, cooled, and diluted with petroleum ether. Diester (B) crystallizes out and is recyrstallized from ethanol-chloroform to give yellow crystals (6.25g, 31%) mp 285°–288° C.

ANALYSIS: Calcd. for $C_{18}H_{15}ClN_2O_6$: C, 55.33; H, 3.87; N, 7.17; Cl, 9.07. Found C, 54.95; H, 3.89; N, 7.08; Cl, 9.37.

A second crop triester (A) crystallizes out and is recrystallized from ethanol-chloroform to give pale yellow crystals (0.80g, 3.5%) mp 175°–178° C.

ANALYSUS: Calcd. for $C_{20}H_{21}ClN_2O_7$: C, 54.99; H, 4.85; N, 6.41, Cl, 8.12. Found C, 54.71; H, 4.88; N, 6.21; Cl, 8.94.

We claim:

1. A compound having the formula IV:

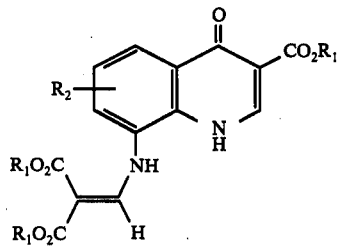

wherein $R_1$ is lower alkyl; and $R_2$ is hydrogen, halogen, lower alkyl or nitro.

2. The compound according to claim 1 which is diethyl ({[3-(ethoxycarbonyl)-1,4-dihydro-4-oxo-8-quinolinyl]amino}methylene)propanedioate.

3. The compound according to claim 1 which is diethyl ({[3-(ethoxycarbonyl)-1,4-dihydro-6-nitro-4-oxo-8-quinolinyl]amino}methylene)propanedioate.

4. The compound according to claim 1 which is diethyl ({[3-(ethoxycarbonyl)-1,4-dihydro-6-methyl-4-oxo-8-quinolinyl]amino}methylene)propanedioate.

5. The compound according to claim 1 which is diethyl ({[3-(ethoxycarbonyl)-1,4-dihydro-6-chloro-4-oxo-8-quinolinyl]amino}methylene)propanedioate.

6. A pharmaceutical composition for treating bacterial infections in mammals comprising an effective amount of a compound of the formula IV:

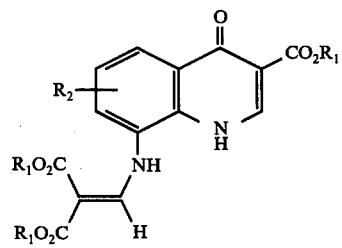

wherein $R_1$ is lower alkyl; and $R_2$ is hydrogen, halogen, lower alkyl or nitro together with an inert pharmaceutical carrier.

7. A method for treating bacterial infections in mammals which comprises the administration of an effective amount of a compound of the formula IV:

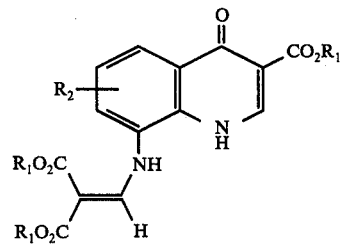

wherein $R_1$ is lower alkyl; and $R_2$ is hydrogen, halogen, lower alkyl or nitro.

* * * * *